United States Patent
Dawson et al.

(10) Patent No.: US 6,515,487 B1
(45) Date of Patent: Feb. 4, 2003

(54) LOW VOLTAGE LOW CURRENT BUBBLE DETECTION CIRCUIT

(75) Inventors: William C. Dawson, Smithtown; Mayank H. Patel, Glen Cove, both of NY (US)

(73) Assignee: Magnetrol International, Inc., Downers Grove, IL (US)

( * ) Notice: Subject to any disclaimer, the term of this patent is extended or adjusted under 35 U.S.C. 154(b) by 0 days.

(21) Appl. No.: 09/644,789

(22) Filed: Aug. 23, 2000

(51) Int. Cl.[7] .................. G01R 27/04; G01R 23/08; G01N 29/02; G01F 1/20; H03F 3/52
(52) U.S. Cl. .................. 324/639; 324/76.51; 73/19.03; 73/861.18; 330/98
(58) Field of Search ............... 324/639, 76.51, 324/76.49; 73/19.1, 19.03, 61.75, 61.79, 861.28, 861.41, 861.18; 330/98, 99, 100

(56) References Cited

U.S. PATENT DOCUMENTS

| | | | | |
|---|---|---|---|---|
| 4,607,520 A | * | 8/1986 | Dam ..................... | 73/19.03 |
| 4,956,877 A | * | 9/1990 | Kroll et al. ............. | 359/170 |
| 5,270,882 A | * | 12/1993 | Jove et al. .............. | 360/67 |
| 5,811,664 A | * | 9/1998 | Whittington et al. ...... | 73/53.04 |

* cited by examiner

Primary Examiner—N. Le
Assistant Examiner—Anjan K. Deb
(74) Attorney, Agent, or Firm—Wood, Phillips, Katz, Clark & Mortimer

(57) ABSTRACT

A low voltage, low current apparatus for detecting discontinuities, such as bubbles, in a fluid stream, in which a tube is placed between a transducer transmitting successive bursts of ultrasonic energy and for receiving the bursts. The receiving transducer is connected to a low current transistor amplifier circuit of a signal processing circuit which keeps an output in a first state when signals are received corresponding to the presence of a fluid and in a second state when the bursts of energy are modified by the discontinuity.

14 Claims, 4 Drawing Sheets

......... = BUBBLE DETECTION CONDITION

_____ = LIQUID DETECTION CONDITION

LOW VOLTAGE LOW CURRENT BUBBLE DETECTION CIRCUIT

FIELD OF THE INVENTION

The present invention relates to a method and apparatus for detecting discontinuities, such as bubbles, in a fluid flow utilizing ultrasonic energy.

BACKGROUND OF THE INVENTION

Various arrangements have been proposed for detecting bubbles in a flow of liquid, particularly where the liquid is in a tubing which is either rigid or compressible. Some of the uses for such a bubble detector would be, for example, in detecting air bubbles in body fluids, such as blood, which are being transmitted from one place to another either with the patient in the transmittal loop or from one type of a machine, such as blood processing machine, to another such machine.

Some known bubble detectors, particularly those detecting on the basis of amplitude of received signal, have a problem in detecting the bubbles caused by the size of the tube in which the fluid flows, the aging of the tube, which reduces its wall thickness and its flexibility, tube wall thickness and also with respect to bubble size. All of these problems give rise to variations in amplitude of the detected received signal. For a constant gain and constant threshold circuit, reliable detection of an air bubble becomes a serious problem.

Dam U.S. Pat. No. 4,607,520, owned by the assignee of the present application, discloses a method and apparatus for detecting bubbles in a stream of liquid flowing in a tube by the use of pulsed ultrasonic energy. Bursts of pulses of ultrasonic energy are transmitted from a transmitting transducer to a receiving transducer. A tube in which the fluid, perhaps containing bubbles, flows is held between the two transducers. The time of arrival of the signals is measured and signal processing is performed to ensure reliable detection. If there are bubbles in the line, then no signals are detected and this state is also detected.

The above described bubble detectors typically operate off a five volt supply and require about 25 milliamps of current. These requirements necessitate use of an appropriate power supply, and effectively preclude its use in battery powered systems.

The present invention is directed to an improvement in the above described bubble detectors.

SUMMARY OF THE INVENTION

In accordance with the invention there is provided a low voltage, low current detection circuit in a novel bubble detector.

A further object is to provide a method and apparatus for detecting bubbles in which pulsed ultrasonic energy is used. Still another object is to provide a bubble detector in which bursts of ultrasonic energy are used and the received bursts are signal processed.

There is disclosed herein an apparatus for detecting a discontinuity in a stream of fluid flowing in a tube. The apparatus includes a sensing means having spaced apart transmitting and receiving transducers, the tube disposed in a space between the transducers. Supply means are provided for connection to a relatively low voltage power source. A discontinuity detection circuit is operatively coupled to the supply means and the sensor. Transmit means supply successive bursts of pulse of electrical energy to the transmitting transducer to cause it to vibrate to produce corresponding bursts of pulses of sonic energy which are transmitted through the tube to the receiving transducer. There is a predetermined time of no pulse production between successive bursts of pulse. The receiving transducer converts the bursts of pulse of received sonic energy into corresponding electrical signals during the predetermined time between the successive bursts. An amplifier circuit is connected to the receiver transducer for amplifying the received electrical signals. The amplifier circuit comprises a transistor amplifier circuit drawing less than about ten milliamps from the supply means. Receive means are responsive to the amplified electrical signals during the predetermined time for producing a first signal corresponding to the pulses of the transmitted pulses of a burst in response to the presence of the fluid and a second signal in response to the presence of a discontinuity in the fluid. Means are responsive to receipt of the first or second signals to produce an output corresponding to the presence of the fluid or a discontinuity in the fluid.

Other objects and advantages of the present invention will become more apparent upon reference to the following specification and annexed drawings.

DETAILED DESCRIPTION OF THE INVENTION

Figure 1:
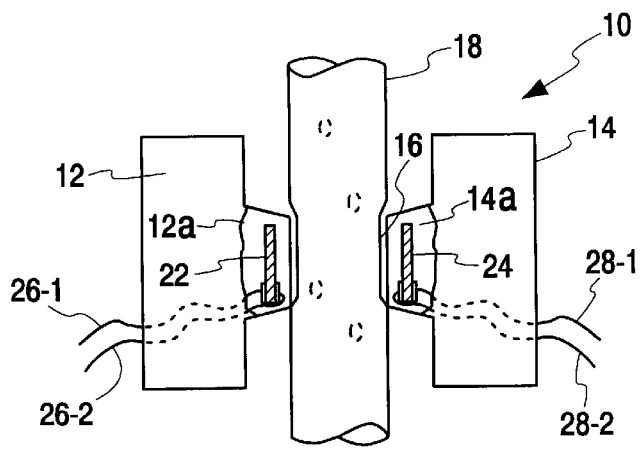
FIG. 1 is an elevational view of the sensing head of the bubble detector according to the invention installed on tubing shown partially broken away.
Figure 2:
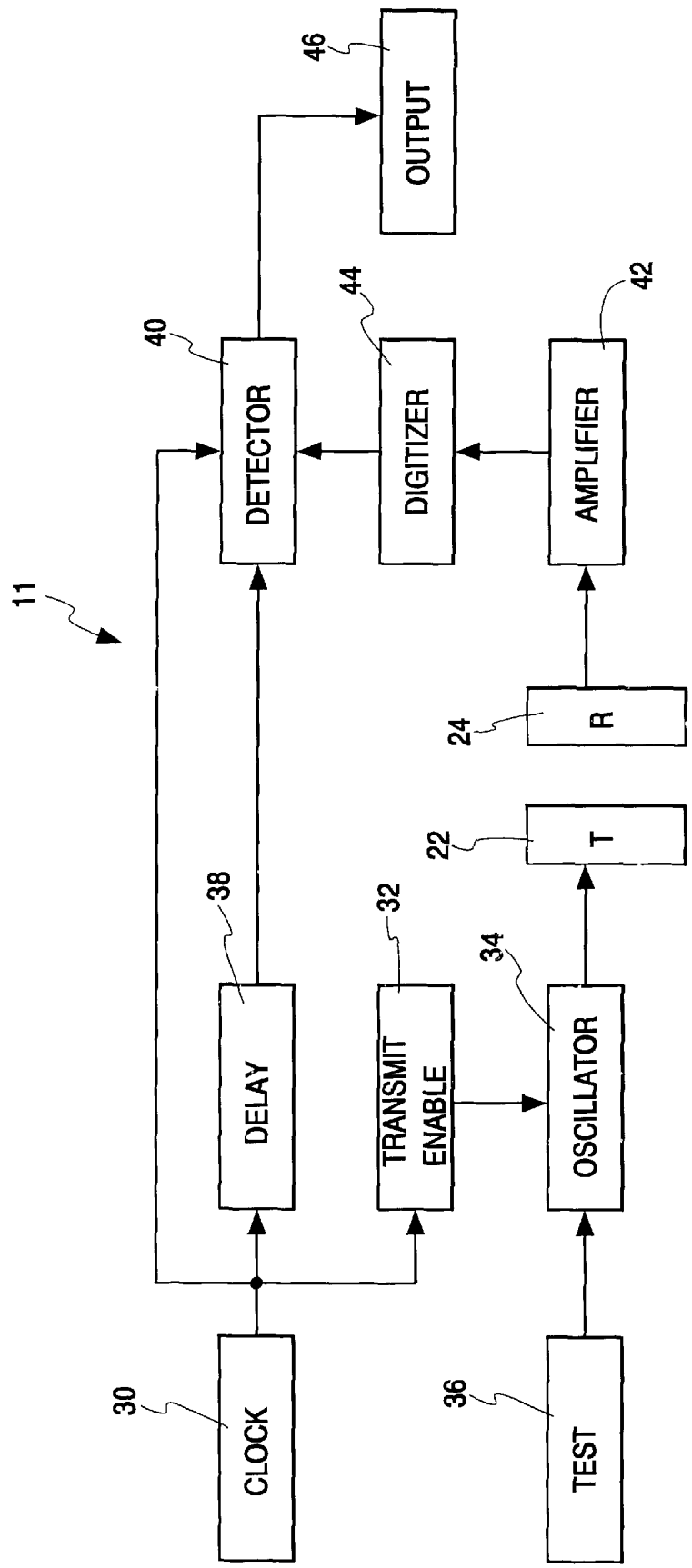
FIG. 2 is a block diagram of the bubble detector according to the invention.

FIG. 1 shows a sensor in the form of a sensing head 10 used in a bubble detector 11, see FIG. 2, according to the invention. The sensing head 10 has two sections 12 and 14. Each section 12 and 14 has a respective projection 12a and 14a forming a space 16 within which a tube 18, for example of compressible plastic material, is placed. A rigid chamber of plastic or glass or other material can be used, if desired. The space 16 between the projections 12a and 14b is selected so that there will be a tight fit for the tube 18 and preferably the portion of the tube 18 held between the two projections 12a and 14a is flattened. By using the arrangement with a compressible tube, the use of ultrasonic energy coupling compound, e.g. silicone grease, can be avoided. If the tubing 18 is of glass or other noncompressible material, then the space 16 is sized to provide a firm fit and coupling compound used.

Each of the sections 12 and 14 has a respective ultrasonic transducer 22 and 24 embedded therein. The transducers 22 and 24 can of any suitable piezoelectric material as is well known in the art, for example, PZT. As is conventional, each transducer 22 and 24 has an electrode on each face and a lead is connected thereto. The leads for the transducer 22 are designated 26-1and 26-2 and for the transducer 24 are 28-1 and 28-2. The leads provide energy to or convey energy from the respectively connected transducer 22 or 24. The sensing head sections 12 and 14 are preferably molded from a suitable material, for example, an epoxy. The transducer elements 22 and 24 and the leads 26 and 28 are also molded within the head sections 12 and 14. The sections of the sensing head can be molded as a one-piece unit with a common back support or as separate pieces and then mounted to a common support.

In describing the invention, the transducer 22 is the transmitter and the transducer 24 is the receiver, as shown in FIG. 2. That is, the transducer 22 receives bursts of electrical energy and converts them into ultrasonic energy which is transmitted through the tube 18 toward the receiving transducer 24. If there is liquid in the tube 18, then the energy is transmitted through the tube 18 and received by the receiving transducer 24 which converts the ultrasonic energy into electrical energy which can be detected by a suitable electronic circuit. If there is a discontinuity in the fluid stream in the tube, for example an air bubble, then there is no signal received. For ease of description, the invention is described with respect to air bubbles in the fluid stream.

The size of the transducers 22 and 24 determines the size of the bubble which can be reliably detected. That is, the surface area of each piezoelectric element is made slightly larger than the minimum size bubble to be detected. The resonant frequency is a function of the thickness of the element. If there is a bubble in the tube 18 which is equal to or larger than the size of the transducer, then there will be no signal received by the receiving transducer 24. It should be understood that the bursts of ultrasonic energy are transmitted at a rate which is substantially greater than the flow rate of the bubbles in the tube so that any stoppage of transmission of the energy through the tube, caused by the presence of an air bubble, is reliably detected.

Referring to FIG. 2, the bubble detector 11 includes a clock pulse generator 30 which produces bursts of ultrasonic energy in the form of rectangular clock pulses at a desired frequency, and for a predetermine period of time. Typical frequencies, for the pulses which have been found to work successfully are in the range of about 3 MHz to about 5 Mz. Other frequencies can be used depending upon the type of liquid to be sensed, the type of tube, the diameter of the tube, etc. While these frequencies may also be considered to be in the low radio frequency range, they are also considered to be ultrasonic in the sense that they are of higher frequency than sound waves and it is the mechanical properties of the energy which is relied upon for transmission through the liquid rather than the electromagnetic properties. The piezoelectric transducer elements 22, 24 are resonant at or near the frequency of the pulses from the clock pulse generator 30.

The clock pulse generator 30 can be on continuously and its pulses are supplied to a transmit enable circuit 32. The transmit enable circuit 32 enables operation of an oscillator 34 connected to the transmitting transducer 22. The transmit enable circuit 32 produces an enable signal for a transmit time window during which the oscillator signal pulses are provided to the transducer 22 for transmission through the tube 18. The duration of the transmit window is selected based upon a variety of factors such as minimum bubble size and flow rate. The window time and repetition rate should be such that at least several bursts of energy will pass through a minimum size bubble as it passes across the transducer surface. The oscillator 34 is alternatively disabled by a remote test input 36.

The clock pulse generator 30 is also connected to a delay block 38. The delay block 38 enables a detector 40. The delay block 38 produces a predetermined delay inhibit period which corresponds to the time it takes to transmit pulses through the tube 18, i.e. corresponds to the tube diameter or overall width for the frequency of the pulses transmitted. This time is known by virtue of knowledge of the tube diameter, liquid flowing in the tube and pulse frequency. During the time the detector 40 is enabled, the receiving transducer 24 is available to listen for received signals which are transmitted through the tube and processing of the received signals is taking place. The output of the delay block 38, when it changes state, turns on the detector circuit 40 to produce a receive window.

Signals received by the transducer 24 from the transducer 22 which are transmitted through the tube 18 when a liquid is present in the tube are converted from acoustic energy into an analog RF signal by the receiver transducer 24. These signals are applied to the input of an amplifier 42. The output of the amplifier 42 is applied to a to a digitizer 44. This is a conventional circuit, which has a pulse shaping, or squaring, circuit. The squaring circuit squares the received signal into pulses which can be processed and counted. The output of the digitizer 44 is applied to the detector circuit 40 whose other input is from the delay circuit 38.

It should be understood that the bursts of energy are transmitted at a relatively high rate which corresponds to the flow rate in the tube, that is, there are a large number of bursts transmitted, say four or more, during the time that a single bubble would be passing across the active surface area of the transducers 22 and 24. This provides a number of cycles of transmitted and received signals so that signal processing can be performed to ensure a more reliable operation for the system than if merely amplitude level detection were utilized.

Assuming that there is liquid in the tube 18, the signals received by the receiver transducer 24 are amplified and converted to pulses by the digitizer 44. These pulses are processed in the detector circuit 40 during the receive window which produces an output pulse to an output circuit 46.

Figure 3A:
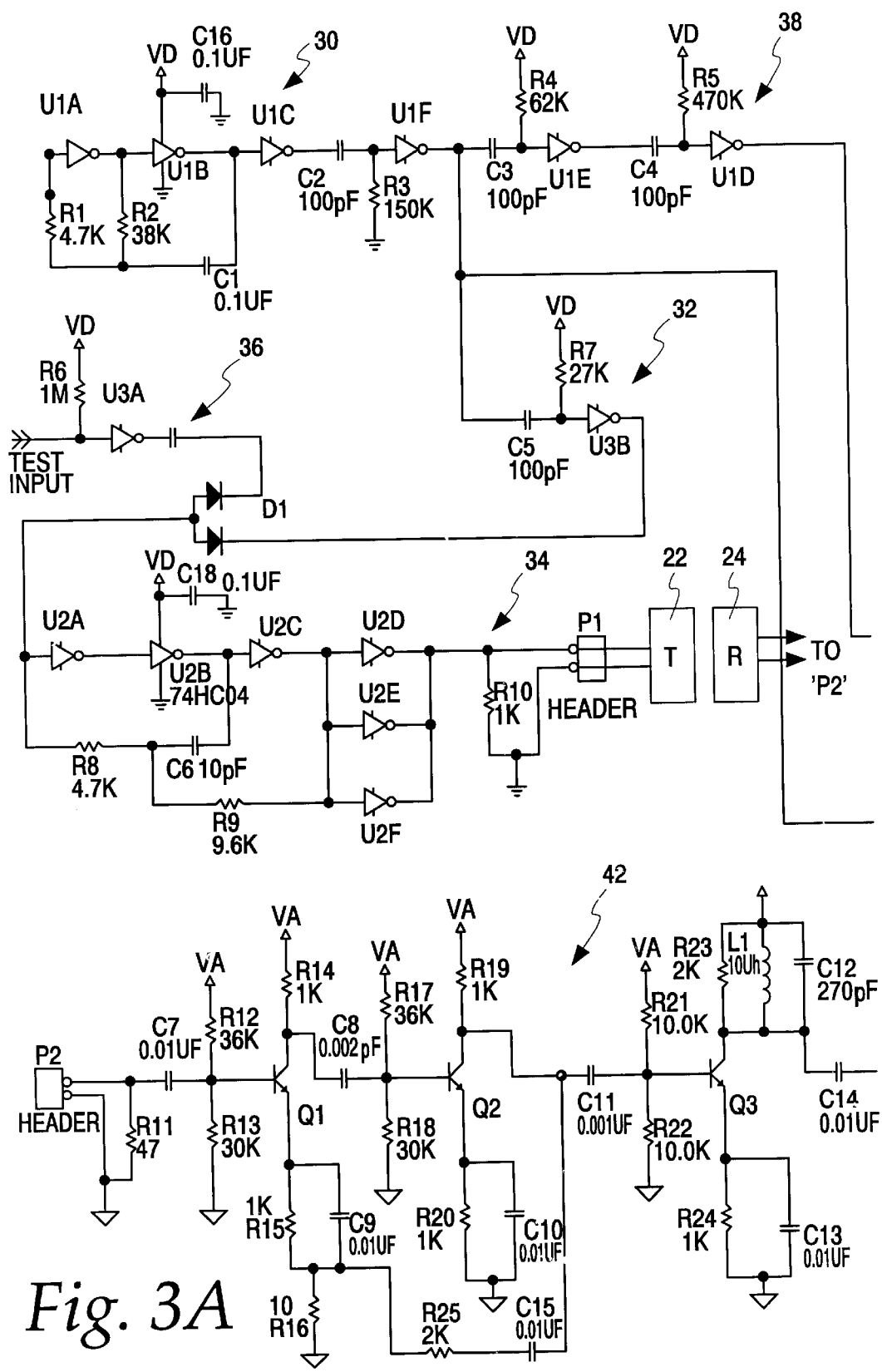
FIG. 3 is an electrical schematic of the bubble detector according to the invention.
Figure 3B:
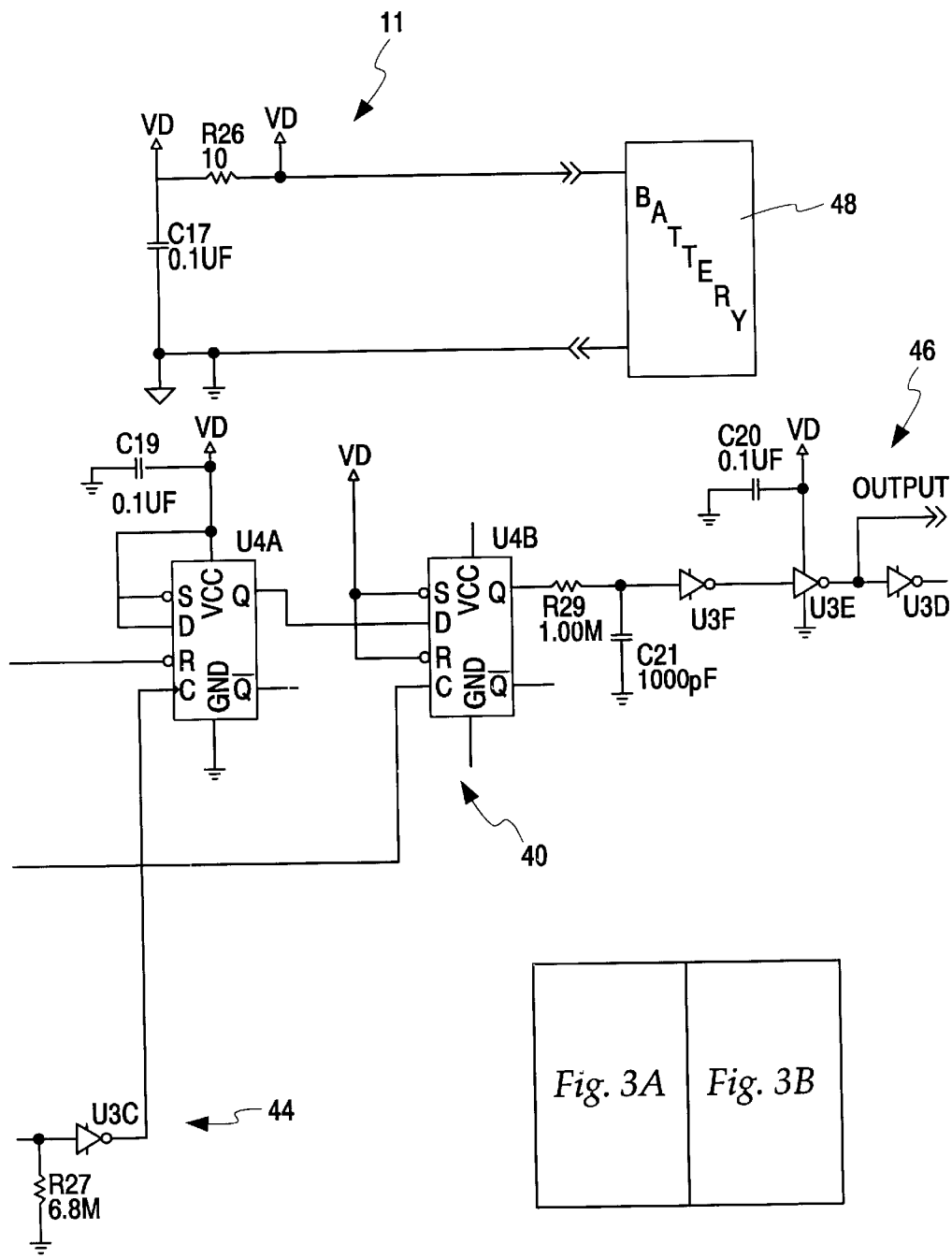

Referring to FIG. 3 an electrical schematic illustrates a circuit for the bubble detector 11. The clock pulse generator 30 includes gates U1A and U1B configured as an oscillator to generate the main clock from all other timing pulses are generated. The frequency of oscillation is 1.4 kHz., +/−15%. The positive half of the main clock keeps a capacitor C2 charged and it discharges through a resistor R3. The values of R3 and C2 are selected so that the pulse width at pin 12 of a gate U1F connected to the junction of the resistor R3 and the capacitor C2 is approximately 11microseconds.

The delay circuit 38 is connected to the output of the gate U1F. A capacitor C3 is connected between the gate U1F and a gate U1E. A capacitor C4 is connected between the gate U1E and a gate U1D. The inputs of the gates U1E and U1D are connected to supply VD through respective resistors R4 and R5. The window delay time and window width time is generated by selecting R4, C3 and R5, C4 respectively.

The transmit enable circuit 32 generates a pulse of approximately 2 microseconds with a duty cycle of 700 microseconds. The transmit enable circuit 32 is connected to the output of the gate U1F. A capacitor C5 is connected between the gate U1F and a gate U3B. The inputs of the gate U3B is connected to supply VD through a resistor R7. The pulse time generated by U3B is determined by selecting R7 and C5.

The transmit enable gate U3B allows the three gate oscillator 34, including gates U2A, U2B and U2C, to produce a 3 MHz signal for approximately 2 microseconds. The frequency of oscillation is set by a capacitor C6, and resistors R8 and R9. The ultrasonic pulses generated are applied to the transmitting transducer 22 through three parallel gate buffers U2D, U2E and U2F. The gate buffers U2D-U2F are connected via a header P1 to the transducer 22.

The transmitted signal passes through the tube 18 and reaches the other side when the tube is filled with liquid where it is converted back to an electrical signal by the receiver transducer 24. The receiver transducer 24 is connected via a header P2 to the amplifier circuit 42. In accordance with the invention, the amplifier circuit comprises a discrete transistor amplifier. The electrical signal from the receiver transducer is amplified by a factor of about one-thousand, but draws minimal current. The amplifier circuit 24 consists of respective first, second and third stage transistors Q1, Q2 and Q3. Feedback in the first and second stages is provided by a capacitor C15 and a resistor R25. The amplifier circuit 24 is tuned to amplify only the 3 MHz frequency signal by an inductor L1 and a capacitor C12. The tuning is done at the third stage, after the feedback. The gain of the amplifier 24 is set to approximately 60dB. The amplifier 42 operates at a voltage of 3 VDC minimum and receives an input in the range of 3.0 to 3.3 VDC. The current drawn by the amplifier circuit 42 is substantially less than ten milliamps and is preferably less than 2.5 milliamps. As a result the input may be supplied by a battery 48 as a power source.

The amplified signal is then digitized in the digitizer 44 by a gate U3C and is used as a clock input for a resettable D type flip-flop U4A of the detector circuit. The delay/window signal generated by the gates U1E and U1D of the delay circuit 38 is connected to a reset pin R of the flip-flop U4A which allows the transfer of data at a data pin D, which is always high, to the Q output pin of U4A upon receiving a clock pulse, representing the received signal, during the window period. The window signal is set to coincide with the signal occurrence timing. Thus any signal prior to the window period, such as digital signals from the transmit signal, is blocked. The Q output of flip-flop U4A is applied to the data input, D, and latched at the Q output of a second resettable D type flip-flop U4B by applying a clock signal from the gate U1F, generated at a predetermined time set by C2 and R3.

The output from the resettable D-type flip-flop U4B is fed to a gate U3F of the output circuit 46 through a time constant set by a resistor R29 and a capacitor C21. The output of the gate U3F is then inverted by a gate U3E to produce the final output.

The test input to a gate U3A must be held at ground potential for the circuit to work normally. If the test input is disconnected, or connected to a 3 VDC source, then the oscillator 34 is disabled. This causes the output to switch to the bubble detected condition, i.e. low if the sensor and electronics are working property.

Figure 4:
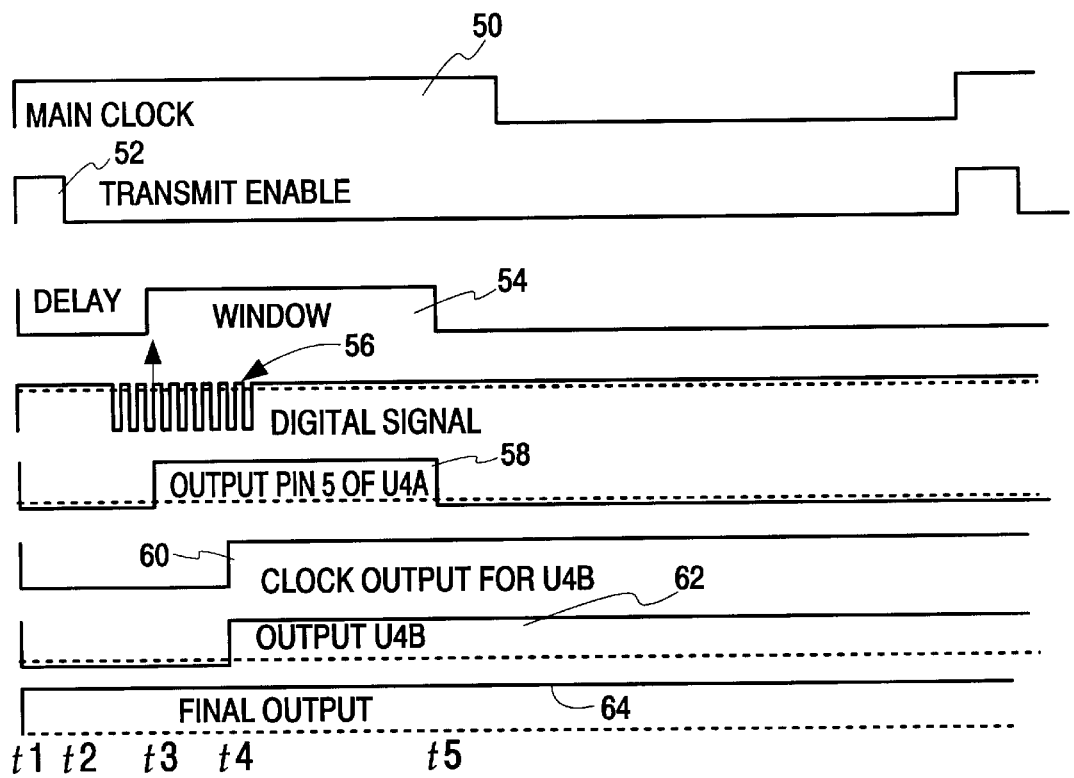
FIG. 4 shows a timing diagram for the bubble detector according to the invention.

The operation of the bubble detector 11 is illustrated in the timing diagram of FIG. 4. The positive half of the main clock pulse 50 begins at a time t1. The transmit enable pulse 52 is initiated by the main clock pulse to enable the oscillator 34 for a shorter time, ending at t2. The delay window 54 begins at a time t3, after the transmit enable pulse 52, and ends at t5. A digital signal from the receiver transducer 24 begins during the delay time and extends into the delay window 54. As shown, the digital signal is a pulse train indicated in solid line for a liquid detection condition and a constant value indicated in dotted line for a bubble detection condition. The Q output of U4A is a pulse 58 for a liquid detection condition. There is no pulse for a bubble detection condition. The clock input for U4B is a pulse 60 beginning at time t4. The clock input passes the Q output of U4A to the output of U4B, as indicated at 62. The final output at 64 remains high for a liquid detection condition and is low for a bubble detection condition.

While the system has been described with respect to detecting air bubbles in a fluid stream, it should be understood that it can also detect solid particles or two different liquids, e.g. drops of slugs of oil or water flowing in a stream of a different liquid, drops of liquid in a gas, etc. As should be apparent, solid particles, the drops of liquid in a gas stream, and a liquid different from the main one have different transmission characteristics to the ultrasonic energy, this will result in different amplitudes of signals being received by the transducer 24. The detector 40 can be set to distinguish between the amplitudes of signals from the two different types of materials flowing in the tube. As used herein, the term discontinuity is used to encompass any such air bubble, particle, different type of liquid, etc.

In accordance with the invention, there is provided a low voltage, low current bubble detector. The bubble detector operates from a supply of 3.0 to 3.3 VDC and draws only about 2.5 milliamps, i.e, substantially less than the prior detector which drew about 25 milliamps. Thus the circuit may be used with battery powered systems.

We claim:
1. An apparatus for detecting a discontinuity in a stream of a fluid flowing in a tube comprising:
a sensor having spaced apart transmitting and receiving transducers, the tube being disposed in a space between the transducers;
supply means for connection to a relatively low voltage power source; and
a discontinuity detection circuit operatively coupled to the supply means and the sensor and including transmit means for supplying successive bursts of pulses of electrical energy to said transmitting transducer to cause it to vibrate to produce corresponding bursts of pulses of sonic energy which are transmitted through said tube to said receiving transducer, there being a predetermined time of no pulse production between successive burst of pulses, said receiving transducer converting the bursts of pulses of received sonic energy into corresponding electrical signals during said predetermined time between said successive bursts, an amplifier circuit connected to the receiver transducer for amplifying the received electrical signals, the amplifier circuit comprising a transistor amplifier circuit drawing less than about ten milliamps from the supply means and receive means responsive to said amplified electrical signals during said predetermined time for producing a first signal corresponding to the pulses of the transmitted pulses of a burst in response to the presence of said fluid and a second signal in response to the presence of a discontinuity in said fluid, and means responsive to receipt of said first or said second signals to produce an output corresponding to the presence of said fluid or a discontinuity in said fluid.
2. Apparatus as in claim 1 wherein the tube is of compressible material, said sensor comprising a sensing head with the transducers fixedly mounted thereon with a space there between into which the tube fits, the head flattening the tube in the area of said transducers to provide coupling of the sonic energy to and from said tube.
3. Apparatus as in claim 1 wherein said bursts of electrical energy are produced at a rate such that at least one burst of source signals is transmitted through a discontinuity of a given size at a given flow rate of fluid.

4. The apparatus of claim 1 wherein the amplifier circuit comprises a three stage amplifier, having first, second and third stages.

5. The apparatus of claim 4 wherein the amplifier circuit includes a feedback circuit.

6. The apparatus of claim 5 wherein the amplifier circuit feedback circuit is in the first and second stages.

7. The apparatus of claim 4 wherein the amplifier circuit includes a tuning circuit tuned to a frequency of the transmitted bursts of pulses.

8. The apparatus of claim 7 wherein the amplifier circuit tuning circuit is at the third stage.

9. The apparatus of claim 1 wherein the amplifier circuit has a gain set to about 60 dB.

10. The apparatus of claim 1 wherein the receive means includes a flip-flop circuit having a clock input receiving the amplified signal, and a data input that is set high, so that the first signal corresponds to an output of the flip-flop being high and the second signal corresponds to the output of the flip-flop being low.

11. The apparatus of claim 10 wherein the receive means is operable to reset the flip-flop at a beginning of the predetermined time.

12. The apparatus of claim 1 wherein the transmit means comprises an oscillator.

13. The apparatus of claim 12 wherein the transmit means comprises a transmit enable circuit that enables the oscillator for a select time prior to a beginning of the predetermined time.

14. The apparatus of claim 1 wherein the relatively low voltage power source comprises a battery.

* * * * *